United States Patent [19]
Karlsson et al.

[11] Patent Number: 5,447,501
[45] Date of Patent: Sep. 5, 1995

[54] NEEDLE PROTECTION DEVICE

[75] Inventors: Jörgen Karlsson; Werner Brandt, both of Helsingborg, Sweden

[73] Assignee: BOC Ohmeda Aktiebolag, Helsingborg, Sweden

[21] Appl. No.: 133,005

[22] PCT Filed: Apr. 13, 1992

[86] PCT No.: PCT/SE92/00249

§ 371 Date: Oct. 8, 1993

§ 102(e) Date: Oct. 8, 1993

[87] PCT Pub. No.: WO92/18182

PCT Pub. Date: Oct. 29, 1992

[30] Foreign Application Priority Data

Apr. 11, 1991 [SE] Sweden .................... 9101102

[51] Int. Cl.⁶ ............................................. A61M 5/32
[52] U.S. Cl. ...................... 604/198; 604/110; 604/263; 128/763
[58] Field of Search .............. 604/188, 263, 198, 192, 604/171, 110, 111, 162, 163, 197, 187; 128/763, 765, 770

[56] References Cited

U.S. PATENT DOCUMENTS

| | | | |
|---|---|---|---|
| 2,679,246 | 5/1954 | Cohen | 604/263 X |
| 4,326,520 | 4/1982 | Alley | 604/163 X |
| 4,725,267 | 2/1988 | Vaillancourt . | |
| 4,770,655 | 9/1988 | Haber et al. | 604/110 |
| 4,838,863 | 6/1989 | Allard et al. . | |
| 4,850,994 | 7/1989 | Zerbst et al. . | |
| 4,908,022 | 3/1990 | Haber . | |
| 4,932,939 | 6/1990 | Magre et al. . | |
| 4,955,866 | 9/1990 | Corey . | |
| 4,973,317 | 11/1990 | Bobrove . | |
| 4,978,343 | 12/1990 | Dysarz et al. . | |
| 4,978,344 | 12/1990 | Dombrowski et al. | 604/198 |
| 4,986,813 | 1/1991 | Blake, III et al. . | |
| 5,015,242 | 5/1991 | Heifetz | 604/198 |
| 5,046,508 | 9/1991 | Weissler | 128/763 |
| 5,122,123 | 6/1992 | Vaillancourt | 604/192 |
| 5,295,963 | 3/1994 | Deeks | 604/110 |

Primary Examiner—C. Fred Rosenbaum
Assistant Examiner—V. Alexander
Attorney, Agent, or Firm—Browdy and Neimark

[57] ABSTRACT

A device for protecting a needle in medical equipment includes a rigid front part connected to a flexible rear part. The front and rear parts surround the needle circumferentially. A locking mechanism accommodated in a chamber provided in the front part. In a position of preparedness, the locking mechanism allows the needle to pass through a hole or in the front part. In an activated position, it presents the needle from passing through. In the position of preparedness, the parts are spaced from the tip of the needle. The locking mechanism is a resilient member which in the position of preparedness is maintained under tension, exerting a force substantially at right angles to the longitudinal direction of the needle, so that the tip of the needle, in the position of preparedness, is supported by the hole or the channel. The resilient member is thus maintained under tension and prevents the needle from passing through the hole after it passes from the position of preparedness to the activated position when the needle is moved rearwards relative to the front part.

19 Claims, 4 Drawing Sheets

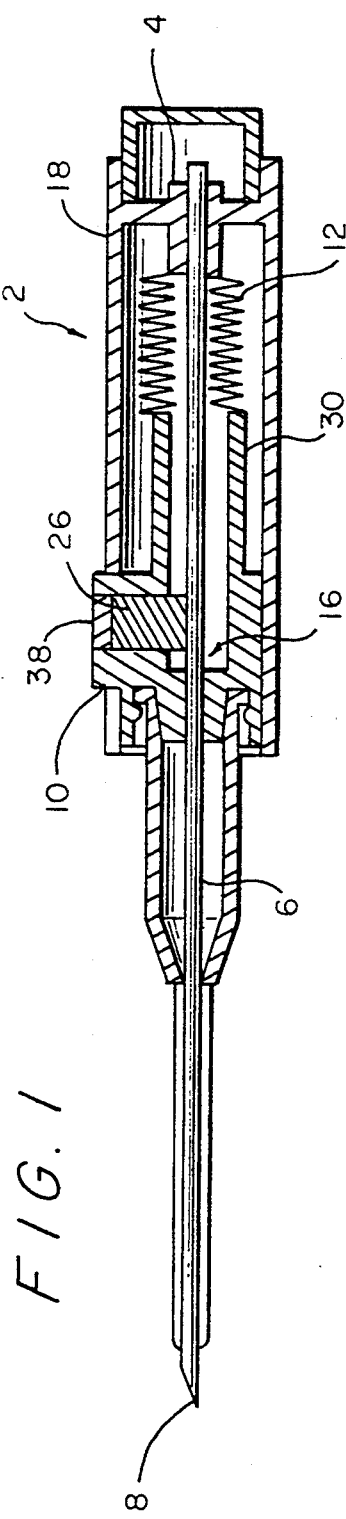
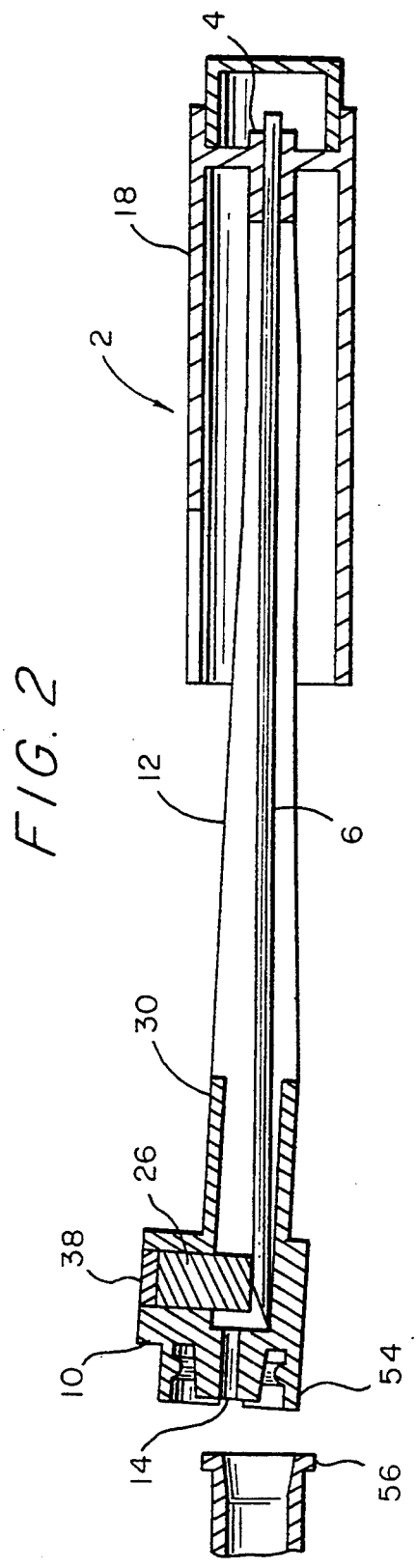

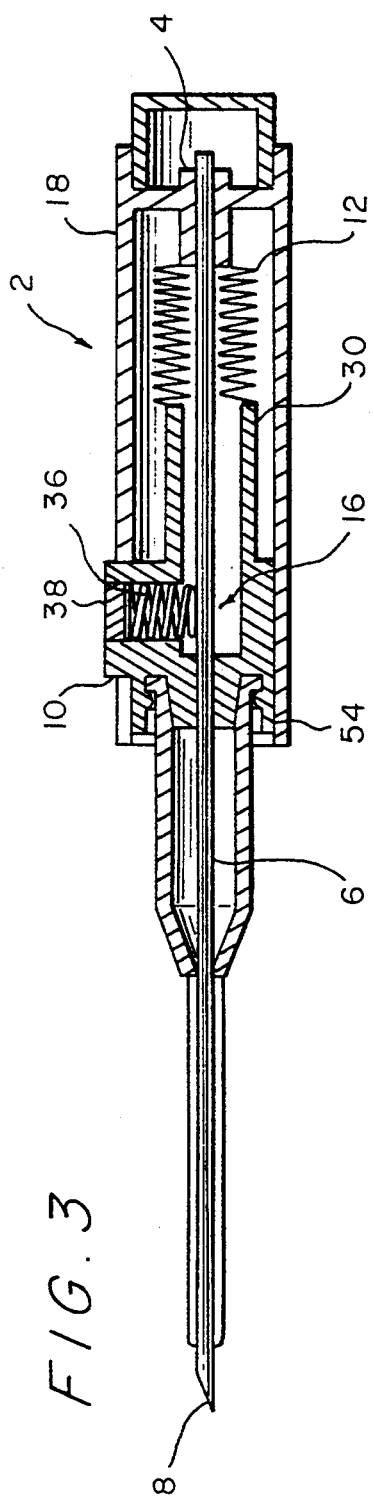
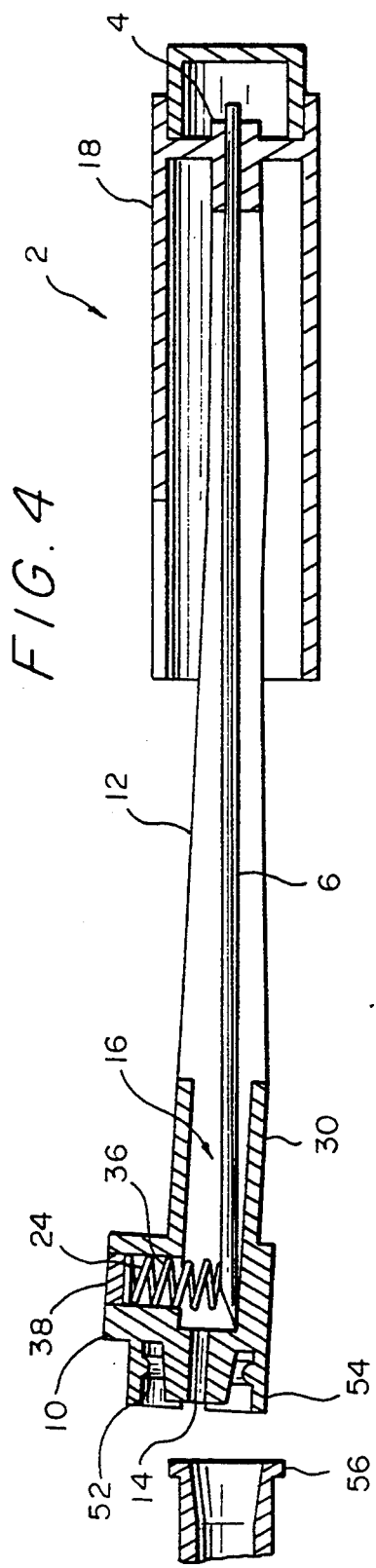

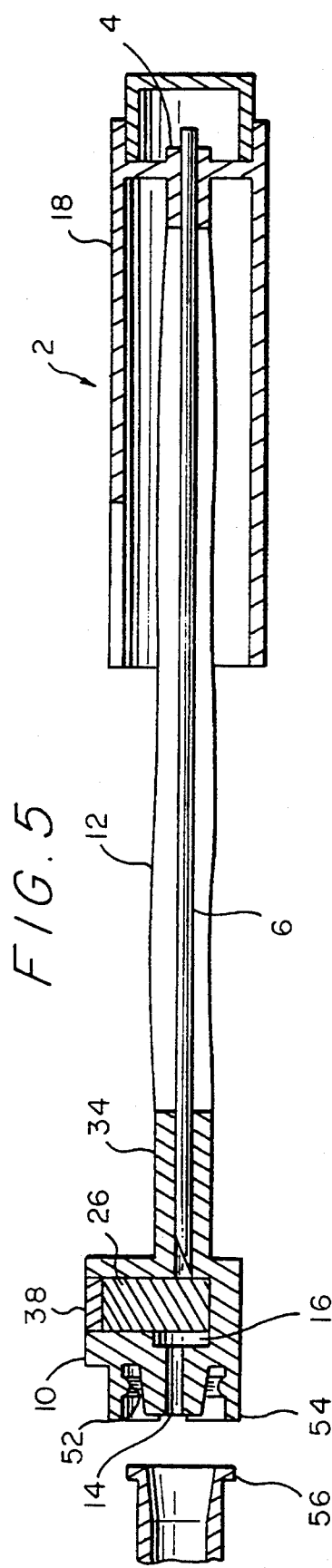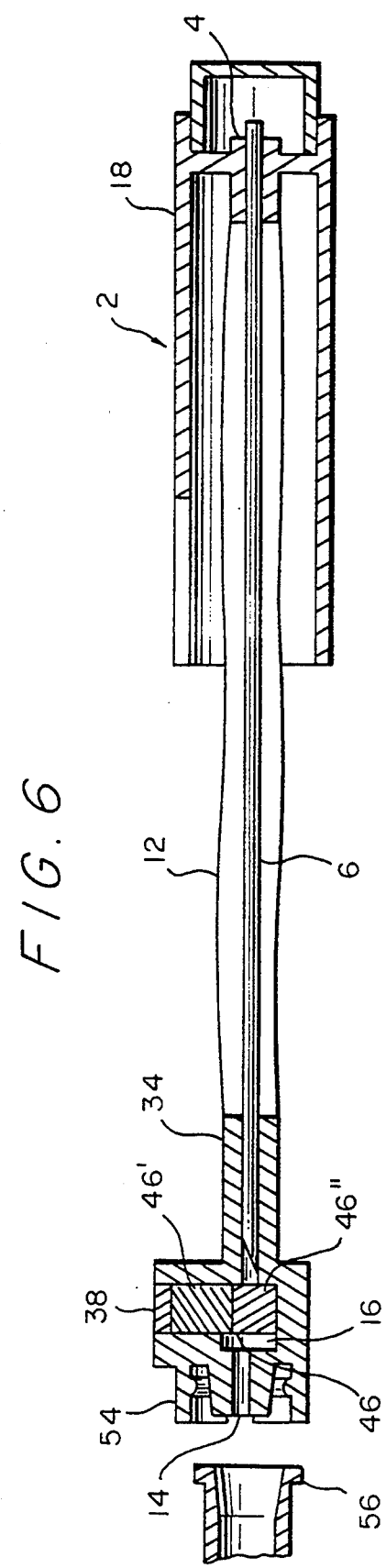

NEEDLE PROTECTION DEVICE

The present invention generally relates to a device for use in infusion cannulas, and more specifically to a device for protecting a needle or the tip of a needle used in such contexts.

The existence of contagious or infectious diseases, such as AIDS and hepatitis B, which via the blood, other body fluids or tissue parts can infect the nursing staff, makes the treatment/care of patients extremely hazardous, since each patient must be regarded as a potential infection source.

Since the discovery of HIV, many people in the health service, ambulance personnel, nurses, doctors and others have been infected, e.g. by body contact with or accidental pricking by infected needles which have been used in the treatment of blood-infected patients.

To protect the nursing staff who is directly involved in the care of such highly infectious patients, extensive efforts have been used for developing syringes and infusion cannulas, as well as protection devices for use in such syringes and infusion cannulas, with a view to preventing direct contact with infected needles and safeguarding against accidental needle pricking.

One example of such a device is disclosed in U.S. Pat. No. 4,725,267, in which a spring-biased needle tip protection means is moved forwards over the needle tip after the needle has been used. The spring actuating the protection device may be integrated with a flexible tube which prevents direct contact with the end of the needle remote from the needle tip.

Another example of a protection device of the above-mentioned type is disclosed in DE-A1-38 08 688. A needle tip protection means connected to a flexible tube is moved forwards over the needle after this has been used, and is so angled as to bring the needle tip into a clamped position inside the protection device. The flexible tube is then pulled over the end portion of the needle remote from the needle tip.

Further, protection devices are known in the art which have no flexible tube, but yet cover, that is surround, the entire needle. One example of such a device is illustrated in U.S. Pat. No. 4,850,994, in which a rigid sleeve-shaped member, which is movable in the longitudinal direction of the needle, is moved, after the needle has been used, over the needle, which then is completely surrounded by the sleeve-shaped member in spaced-apart relationship thereto.

U.S. Pat. No. 4,955,866 discloses a needle tip protection means which is in the form of a cylindrical part surrounding the needle. The cylindrical part is fixed, e.g. by a thread, to the end of the needle remote from the needle tip. This part may be formed with a chamber provided with a washer having a hole through which the needle passes in the position of use. After the needle has been used, the cylindrical part is manually moved over the needle tip, the needle being retracted from the hole in the washer which thus descends, obstructing the passage in the cylindrical part.

Further, it is known from WO90/08564 to replace the washer traversed by the needle, with a gravity-actuated ball provided in a chamber and serving to prevent exposure of the needle after use.

In addition to sleeve-shaped members which are applied in some suitable manner over the needle tip for protecting it after the needle has been used, it is also known to act on the end of the needle remote from the needle tip, i.e. the mounting end of the needle, such that the needle is made, after use, to form an angle with the axis of the sleeve-shaped member. Examples of this type of approach are given in U.S. Pat. No. 4,770,655, where the needle is also deformed, and in U.S. Pat. No. 4,83,863, U.S. Pat. No. 4,908,022, U.S. Pat. No. 4,932,939, U.S. Pat. No. 4,978,343, and U.S. Pat. No. 4,986,813.

Present-day techniques thus offer a large number of more or less complex solutions for protecting nursing staff and others from used, sometimes contaminated needles. However, since all the known solutions suffer from more or less serious drawbacks, further technical development in this field is indeed called for. Above all, it is the risk of unintentional or deliberate exposure of the used needle after actuation of the needle protection means that should be minimised by developing technically efficient, viable solutions, automatically implemented in connection with the normal handling of the needle and the infusion cannula.

Common to all protection means using a flexible, extensible tube, hose or the like, or a rigid, movable sleeve element is that they are pulled or pushed over the entire needle from the needle end opposite the needle tip. For this reason, the protection means of the above-related type have channels or holes allowing the needle to pass through before the needle is used.

One of the most serious problems encountered in most of the known devices is that the protection means must be applied manually, that is, be pushed or pulled forward along the needle, after this has been withdrawn from the blood vessel or tissue of the patient, where it may have become contaminated, the user holding the needle supporting member in one hand while applying the protection device with the other. It will be appreciated that the risk of injuries from the sharp needle tip or contagion by direct contact with infected blood or infected tissue, by inadvertence, carelessness or even malfunction of the protection device is at a maximum if the protection device must be made operative by an active intervention with the free hand, falling outside the normal handling of the device, after the needle has been removed.

Another problem inherent in the prior-art devices is that the protection device in some cases is so designed that the needle protection means can be unintentionally or deliberately retracted so as to expose the, possibly, contaminated needle. This problem has been encountered in protection devices with actuated as well as unactuated needle connection.

A considerable drawback is that most of the prior-art solutions are complex and of impractical design, entailing relatively high production costs.

A first object of the present invention therefore is to provide a device which is adapted to protect the entire needle and which is automatically made operative in normal handling when the needle is retracted from a blood vessel or tissue of a patient.

A second object of the present invention is to provide a device for protecting the entire needle so as to prevent direct contact with the needle once it has been retracted from a blood vessel or tissue of a patient.

A third object of the invention is to design the needle protection means so as to provide safety against unintentional or deliberate exposure of, primarily, the needle tip, once the protection device has been activated.

A fourth object of the invention is to design the needle protection device so as to prevent the needle, in cases of incorrect use, from being unintentionally removed or the needle tip from being exposed.

Moreover, the device according to the invention should be usable in different types of infusion cannulas, and have a simple and cost-effective design.

Other features and alternative embodiments will appear from the dependent claims.

Embodiments of the present invention will be described in more detail hereinbelow with reference to the accompanying drawings.

FIG. 1 is a sectional view of a schematically illustrated infusion cannula with an inventive protection device in a position of preparedness.

FIG. 2 is a sectional view, similar to FIG. 1, of the schematically illustrated infusion cannula after it has been used, with the inventive protection device in activated position.

FIG. 3 is a sectional view, similar to FIG. 1, of a schematically illustrated infusion cannula, with a preferred embodiment of the inventive protection device in a position of preparedness.

FIG. 4 is a sectional view, similar to FIG. 2, of the preferred embodiment shown in FIG. 3, after the schematically illustrated infusion cannula has been used, with the inventive protection device in activated position.

FIGS. 5 and 6 illustrate other embodiments of a locking means according to the invention.

Figure 7:
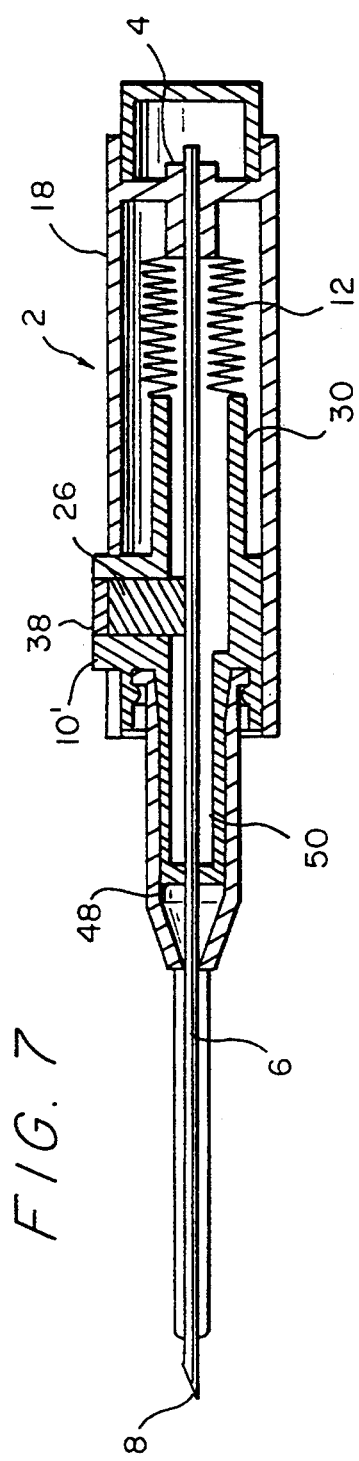
FIG. 7 illustrates an alternative way of designing the front part of the infusion cannula.

FIGS. 1 and 2 illustrate a first embodiment of an inventive protection device arranged in an infusion cannula 2, schematically illustrated. Within the infusion cannula 2 there is a mount or anchorage 4 for a needle 6 having a pointed tip 8. It is understood that the needle can be used with different types of syringes, such as infusion cannulas.

The protection device according to this first embodiment comprises a rigid front part 10 and a rear, flexible part 12 which individually and Jointly surround the needle 6 circumferentially. Both the front and the rear part 10 and 12, respectively, are movable in the longitudinal direction of the needle 6. To this end, the front part 10 has a channel 14 (see FIG. 2) extending through the front part 10, coaxially with the longitudinal axis of the needle 6. Preferably, the channel 14 has a circular cross-sectional profile with an inner diameter equal to or slightly exceeding the outer diameter of the needle 6.

The front part 10 is formed with a chamber 16 through which the needle 6 passes.

A locking means is disposed in a pocket or recess 24. In the illustrated embodiment, the locking means is an elastic, axially compressible body 26 which in the position of preparedness of the device is in a compressed state in the recess 24 (see FIG. 4).

The front part 10 is connected in conventional manner to the rear, flexible part 12 through a socket or tubular extension 30, whose length is adapted to the length of the needle 6 and the casing 18.

In the illustrated embodiment, the rear, flexible part 12 consists of a thin, film-like flexible material which is in the form of a tube or a hose, both ends of which are open. The ends are fixed to the front part 10 and to the needle mount 4. In the position of preparedness, the flexible hose 12 is located inside the casing 18, the thin hose material allowing tight compaction, thus minimizing the extent of the hose in the longitudinal direction of the needle in the position of preparedness of the protection device. Further compaction can be achieved if the hose 12 is given a conical or cornet-shaped form, as indicated in FIG. 2, in which case the hose can be compressed like a spiral into a thin, discold body. The same effect is attained if the hose 12 is bulging, preferably in its central region. The hose 12 has such a length that, in the activated state of the protection device, the needle tip 8 is located, when in its retracted position, inwardly of the channel 14, i.e. In the chamber 16 or inside the socket or tubular extension 30.

In this manner, the entire needle 6 will be efficiently protected, both by the hose 12 surrounding the needle and by the front part 10 enclosing the needle tip 8.

FIGS. 3 and 4 illustrate a second, preferred embodiment of the inventive protection device. The difference between this embodiment and that shown in FIGS. 1 and 2 is the design of the locking means, here designated 36, which is disposed in the front part 10. The remaining components are essentially similar and therefore have been given the same reference numerals, For a detailed description of these components, reference is made to the foregoing description of the first embodiment.

The locking means 26 and 36 operate in substantially the same manner, as will appear from the following description. As appears from FIGS. 1-4, the recess 24, in which the locking means 26 or 36 is located, is provided in the vicinity of the end of the channel 14 which is remote from the channel mouth. When the needle tip 8, by a relative movement between the needle 6 and the front part 10, is moved to a location behind the end of the channel 14 remote from the channel mouth, the tip end of the needle is no longer supported by the channel 14, but the front end portion of the needle 6 is acted on in a region in the immediate proximity of the needle tip 8, and the force exerted by the locking means 26 or 36 essentially at right angles to the longitudinal axis of the needle results in a deflection of the needle 6 away from the longitudinal direction of the device, thus preventing the needle from passing into the channel 14. It is then preferred to limit the relative movement between the needle 6 and the front part 10, such that the needle tip 8 occupies a position in the chamber 16 or the tubular extension 30 immediately below the recess 24 accommodating the locking means 26 or 36. This limitation of the path of movement of the needle is suitably brought about by giving the hose 12 such a length that the needle tip 8 can be retracted just out of the end of the channel 14 remote from the channel mouth.

FIGS. 5 and 6 illustrate variants of the embodiment, described with reference to FIGS. 1-4, of the front part 10 of the protection device when in activated position. Also in this embodiment, the front part 10 has a chamber 16 communicating with the recess 224 accommodating a locking means 26, described with reference to FIGS. 1 and 22, or a locking means 46 (see FIG. 6), which will be described in more detail hereinbelow. The chamber 16 passes into a tubular extension 34 extended in the longitudinal direction of the device and having a diameter equalling or but slightly exceeding the outer diameter of the needle 6. While perfectly guiding the needle 6, the narrow, tubular extension 34 at the same time excludes the possibility of deflecting the needle 6 away from the longitudinal axis of the device, as described by way of introduction. Therefore, the rear, flexible part 12 is given such a length that the needle tip 8, after completed rearward movement in relation to the front part 10, is brought to a position within the tubular extension 34. Once the needle tip 8 has passed backwards through the chamber 16, which in normal handling occurs by retraction of the needle 6, after the front part of the infusion cannula has been fixed, the locking means 226 or 46 expands substantially in its longitudinal direction and extends between the bottom of the recess 24 and the portion of the chamber 16 opposite the recess bottom, so as to obstruct the channel 14, thus preventing the needle 6 from passing into the channel 14.

In FIG. 5, the locking means consists of the elastic body 26, described with reference to FIGS. 1 and 22, which is compressible in its longitudinal direction. It is made of any suitable material, such as silicone. It is understood that the needle 6, by the exertion of a sufficiently great force in the axial direction, can be caused to pass through the elastic body 26 and into the channel 14. In this embodiment of the front part 10, it is therefore preferred to use the locking element 46 of FIG. 6. The locking element 46 has at least one compressible, elastic portion 46' and one rigid, impenetrable portion 46". These portions are so arranged in relation to each other that the rigid portion 46", in the activated position of the protection device, is brought into such a position that at least the opening of the channel 14 is obstructed, thus preventing the needle from passing into the channel 14 after the protection device has been activated. The elastic portion 46' may then be a silicone body, a spring or any other suitable element.

FIG. 7 shows yet another alternative embodiment of the front part 10. The channel 14 described above is here replaced by a through hole in an end wall 48, facing the needle tip 8, of an elongate cavity 50 which, as in the previous embodiments, communicates with the recess 24 accommodating the locking means, in this case a locking means 26 of the type described by way of introduction, and with the tubular extension. The advantage conferred by the embodiment of FIG. 7 appears clearly. As a major part of the needle 6 is surrounded by, here, the more extended front part 10' and the rear part 12 already in the position of preparedness of the device, the distance through which the needle 6 must be moved rearwards relative to the front part 10' will be considerably shorter than in the embodiments described above. This means that the protection device is made operative earlier in connection with the normal handling of the cannula. Although the force exerted by the locking means on the needle 6 no longer affects the area in the immediate proximity of the needle tip 8, it has been found that this force is sufficient for deflecting the needle away from the longitudinal direction of the device, or deflecting the front part 10', 10' away from the longitudinal direction of the needle, whereby to, again, prevent the needle from passing through the hole in the end wall 48 of the front part 10'.

Figure 8:
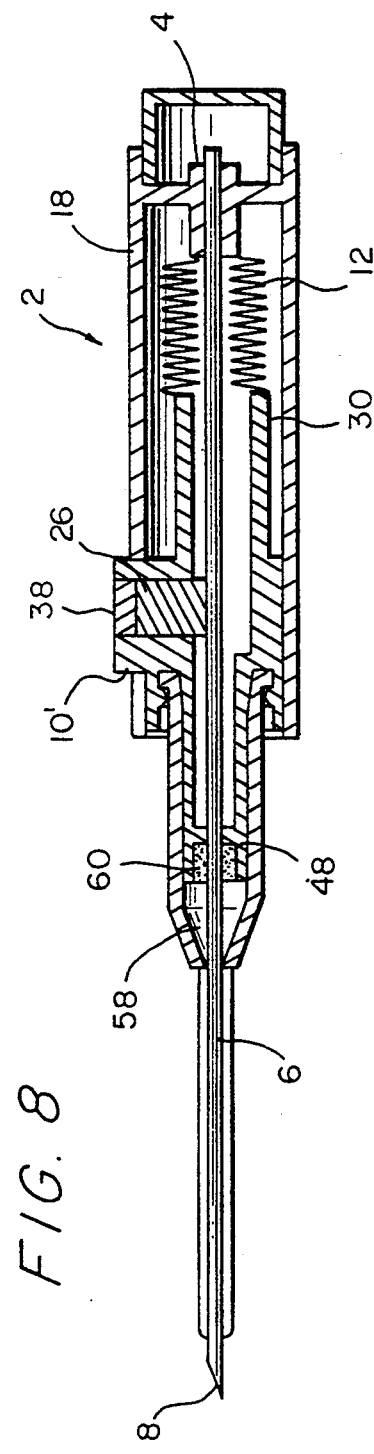
FIG. 8 is a sectional view, similar to FIG. 7, where the front part of the infusion cannula is provided with a chamber in which blood that may adhere to the needle is collected.

FIG. 8 illustrates a variant of the embodiment in FIG. 7. The features of the embodiment in FIG. 8 are however also applicable to other embodiments. In this case, the elongate cavity is slightly shorter as compared with the embodiment of FIG. 7. At the side of the wall 48 facing the needle tip 8, there is provided a chamber 58 circumferentially surrounding the needle 6 which passes through the chamber. In the chamber 58 there is disposed an absorbent material, here a felt 60. The advantage of this arrangement is that any blood that may adhere to the needle 6 is efficiently intercepted and absorbed by the felt 60 in the chamber 58 in connection with the relative movement between the needle and the cannula. In activated position, the needle tip 8 thus is located at the side of the wall 48 facing away from the chamber 58. Any blood adhering to the needle has been efficiently taken up by the absorbent material 60 in the chamber 58 and, hence, does not constitute any hazard.

As appears from FIGS. 1-8, the bottom of the recess 24 consists in all the cases of a seal or a cover 38, for instance a snap cover, to facilitate the mounting of the locking means (the spring 36 or the body 26 or 46), which is suitably mounted after the needle 6 has been inserted in the channel 14, after which the cover 38 is applied on the outside of the device, such that the locking means will be mounted under tension between the needle 6 and the cover forming the bottom of the recess.

For engaging, e.g. a catheter unit, the front part 10 has resilient, circumferentially spaced fingers 54 provided with a bead or a lug 52 (see e.g. FIG. 4) and extended in the longitudinal direction of the device. The lugs 52 which in the position of preparedness of the infusion cannula have been moved over an annular flange 56 of the cannula unit will thus lock this unit to the front part 10. The front part 10 being made of a plastic material, the fingers 54 have a certain flexural elasticity and can thus be disengaged from the annular flange of the cannula unit. When the front part 10 is engaging the cannula unit, the casing 18 can be retracted until the rear, flexible part 12 is stretched, without disengaging the device from the cannula unit. Before the rear part 12 comes to its fully stretched position, in which it can transmit tractive forces, the needle protection device has been activated. When an additional tractive force is applied to the casing 18, the front part 10 is thus disengaged from the cannula unit. The casing 18 has such an inner diameter and such an extent in the longitudinal direction that, in the position of preparedness of the infusion cannula, i.e. before use, it encloses the front part 10. In this manner, the risk of incorrect use is minimised in the normal handling of the infusion cannula. Designing the means for mutual locking of the cannula unit and the front part 10 as individual, cantilevered fingers 54 confers increased safety against incorrect use. If the front part is exposed by moving the casing 18 rearwards only a short distance, the front part 10 might be disconnected from the cannula unit before the needle protection device is activated, i.e. before the needle 6 is located in the chamber 16 or cavity 50 or in the tubular extension 34. However, if the user grips the front part 10 in the area of the fingers 54, a pressure is exerted on each finger, so as to further increase the locking effect.. In this manner, the needle is efficiently prevented from being exposed by incorrect use.

The invention has thus provided an infusion cannula in which the protection device is automatically activated during normal handling, i.e. when the needle is withdrawn from a blood vessel or tissue of the patient. Hence, the first object has been met.

In the activated position of the protection device, the entire needle is covered by the rear, flexible part and by the front part, the needle tip being safely kept within the rigid, front part, thus preventing direct contact between the needle, which may be contaminated, and exposed body parts of the nursing staff.

The deflection of the needle or the channel in the front part away from the longitudinal axis of the device, or obstruction of the channel opening, together with the other constructional features affords good safety against unintentional or deliberate exposure of the needle tip, once the protection device is activated.

Designing the means for mutual locking of the front part and the cannula unit as cantilevered fingers increases safety against exposure of, primarily, the needle tip, also in case of incorrect use of the infusion cannula.

It is understood that a person skilled in the art may find alternative embodiments and carry out modifications within the scope of the basic inventive concept. Thus, the compressible body or the helical spring can be replaced by a leaf spring applied e.g. In the tubular extension, or by a helical spring through which the needle passes. All such modifications and alterations are therefore intended to be covered by the scope of protection of this invention.

We claim:

1. A needle-protecting device, comprising:
    a needle (6) extending from the device in a forward direction when un-protected, said needle having a tip (8) at a forward end thereof;
    a rigid front part (10) including a chamber (16) therein and a hole (14) in said front part (10);
    a flexible and extensible rear part (12) connected to said front part, said rear part extensibly movable relative to said front part between a position of preparedness and an activated position, said front part and said rear part when in the position of preparedness surrounding the needle circumferentially and being spaced from a tip (8) of the needle (6);
    means for locking disposed within the chamber (16) and coupled to said front part, said means for locking in said position of preparedness allowing the needle (6) to pass through the hole (14) and in the activated position of said front part and said rear part preventing the needle (6) from passing through the hole (14), said means for locking including a resilient member (26; 36; 46) which in said position of preparedness is under tension, exerting a force substantially at right angles to a longitudinal direction of the needle (6);
    a portion of the needle being supported by said hole (14) in the front part (10) such that the resilient member (26; 36; 46) is maintained under tension in said position of preparedness, and after the front part and the rear part pass from the position of preparedness to the activated position and the needle (6) is moved rearwards relative to the front part (10) the resilient member (26; 36; 46) prevents the needle (6) from passing through said hole (14).

2. The device according to claim 1, wherein:
    the front part (10) includes a tubular extension (30) extending in a rearward direction from said front part, said chamber (16) including an interior of said tubular extension, said interior communicating with said hole (14);
    said tubular extension (30) has an inner diameter considerably exceeding an outer diameter of the needle (6);
    said chamber (16) includes a recess (24) disposed alongside of and communicating with the tubular extension (30); and
    wherein the force exerted by the resilient member (26; 36; 46) on the needle (6) in the activated position, wherein the needle is no longer supported by the hole (14), causes an angular disposition between a longitudinal axis of the front part (10) and the needle (6).

3. The device according to claim 2, further including a cannula unit and wherein the front part (10) at a forward side thereof includes fingers (54) extending in the longitudinal direction of the device, the fingers circumferentially spaced apart and including respective beads (52) extending substantially inwards towards an axis of the device, the beads being adapted to engage an annular flange (56) of the cannula unit having an outer diameter, whereby the front part (10) is detachable from the cannula unit by the application of a sufficiently great traction pull.

4. The device according to claim 2, wherein the recess (24) is closed from the outside of the device by a cover (38) so that the resilient member (26; 36; 46) can be easily mounted in the recess (24).

5. The device according to claim 4, wherein the front part (10) at a forward side thereof is provided with fingers (54), each finger (54) has a lug or bead (52) extending substantially inwards towards the axis of the device and adapted to engage an annular flange (56) of a cannula unit, and that the front part (10) is detached.

6. The device according to claim 5 wherein the resilient member comprises at least one part (46′) which is compressible in its longitudinal direction, and one rigid, impenetrable part (46″), the length of the compressible part (46′); in activated position being such that the rigid part (46″) obturates the passage of the needle (6) to the hole (14).

7. The device according to claim 1, wherein:
    the front part (10) includes a tubular extension (34) rearward of said hole (14), said tubular extension (34) having an inner diameter which but slightly exceeds an outer diameter of the needle (6);
    the tubular extension (34) supports the needle (6) both in the position of preparedness and in the activated position; and
    in the activated position the resilient member (26; 46) extends, transversely to the longitudinal direction of the device, between a first side wall of the chamber (16) and a second opposing side wall of the chamber (16) which includes a recess (24), such that a passage to the hole (14) is covered.

8. The device according to claim 7, wherein
    the rear part (12) is connected to the tubular extension (30; 34) and to a casing (18) enclosing an attachment or mount (4) for the needle (6),
    the rear part (12) has a length such that the tip (8) of the needle is located within the front part (10) when the rear part (12) is stretched, and
    wherein the recess (24) is closed from the outside of the device by a cover (38), so that the resilient member (26; 36; 46) can be easily mounted in the recess (24).

9. The device according to claim 8, including a wall (48) of the chamber (16), the hole (14) being disposed through the wall (48) forward of the means for locking (26; 36; 46); a cavity (50) being formed between said wall (48) and the tubular extension (30; 34).

10. The device according to claim 9, including:
    an absorbent material (60) disposed in a circumferential-chamber (58) surrounding the needle in the position of preparedness, the circumferential-chamber being disposed adjacent a forward end of the hole (14) for sucking up any blood that may adhere to the needle (6).

11. The device according to claim 10, wherein the front part (10) at a side remote from the tubular extension (30; 34) includes fingers (54) having a bead (52) extending substantially inwards towards an axis of the device and adapted to engage an annular flange (56) of the cannula unit, and that the front part (10) is detachable.

12. The device according to claim 11, wherein the resilient member is a longitudinally-compressible body (26) selected from the group consisting of silicone rubber and other elastomers.

13. The device according to claim 12, wherein the resilient member comprises at least one part (46') which is longitudinally compressible, and one rigid, impenetrable part (46"), the length of the compressible part (46') in activated position being such that the rigid part (46") obturates the passage of the needle (6) to the hole (14).

14. The device according to claim 1, wherein:
the front part (10) includes a tubular extension (30; 34);
the rear part (12) is connected to the tubular extension (30; 34) and to a casing (18) enclosing an mount (4) for the needle (6); and
the rear part (12) has a length such that the tip (8) of the needle is located within the front part (10) when the rear part (12) is extended.

15. The device according to claim 1, further including:
a wall (48) of the chamber (16), the hole (14) being disposed through the wall (48) and distal the means for locking (26; 36; 46);
a tubular extension (30; 34) of the front part (10); and
a cavity (50) being formed between said wall (48) and the tubular extension (30; 34).

16. The device according to claim 1, wherein:
the rigid front part (10) includes a circumferential-chamber (58) surrounding the needle in the position of preparedness, the circumferential-chamber being disposed adjacent a forward end of the hole (14); and further including
dry material for absorbing liquids (60) disposed within the circumferential-chamber (58) for sucking up blood that may adhere to the needle (6).

17. The device according to claim 1, wherein the resilient member is a lengthwise-compressible body (26) of elastomeric material; the elastomeric material selected from the group consisting of silicone rubber and other elastomers.

18. The device according to claim 1, wherein the resilient member is a lengthwise-compressible spring (36).

19. The device according to claim 1, wherein the resilient member comprises at least one lengthwise-compressible body (46') and one rigid impenetrable part (46"), a length of the compressible part (46') in the activated position being such that the rigid part (46") obturates a passage of the needle (6) to the hole (14).

* * * * *